United States Patent [19]

Schläpfer

[11] Patent Number: 5,190,543

[45] Date of Patent: Mar. 2, 1993

[54] ANCHORING DEVICE

[75] Inventor: Johannes F. Schläpfer, Glarus, Switzerland

[73] Assignee: Synthes (U.S.A.), Paoli, Pa.

[21] Appl. No.: 796,797

[22] Filed: Nov. 25, 1991

[30] Foreign Application Priority Data

Nov. 26, 1990 [CH] Switzerland ............... 03733/90

[51] Int. Cl.$^5$ ............... A61F 5/04; A61F 5/02
[52] U.S. Cl. ............... 606/61; 606/72; 606/69
[58] Field of Search ............... 403/121, 117, 87, 59; 606/60, 61, 73, 90, 65, 72, 69

[56] References Cited

U.S. PATENT DOCUMENTS

| 1,880,446 | 10/1932 | Hem ............... 403/121 |
| 2,686,070 | 8/1954 | Booth ............... 403/117 |
| 4,180,345 | 12/1979 | Routens ............... 403/121 X |
| 4,218,809 | 8/1980 | Zimmermann ............... 403/117 X |
| 4,887,596 | 12/1989 | Sherman ............... 606/73 X |
| 4,946,458 | 8/1990 | Harms et al. ............... 606/61 |
| 4,950,269 | 8/1990 | Gaines, Jr. ............... 606/61 |
| 5,030,220 | 7/1991 | Howland ............... 606/73 X |
| 5,042,982 | 8/1991 | Harms et al. ............... 606/61 |

FOREIGN PATENT DOCUMENTS

| 0392927 | 10/1990 | European Pat. Off. ............... 606/61 |
| 9101691 | 2/1991 | World Int. Prop. O. ............... 606/61 |

Primary Examiner—Robert A. Hafer
Assistant Examiner—Brian E. Hanlon
Attorney, Agent, or Firm—Davis Hoxie Faithfull & Hapgood

[57] ABSTRACT

A pedicle screw or hook has a slotted head for receiving a support rod. A support element in the head transverse to the slot provides limited pivotal movement for the support rod.

17 Claims, 2 Drawing Sheets

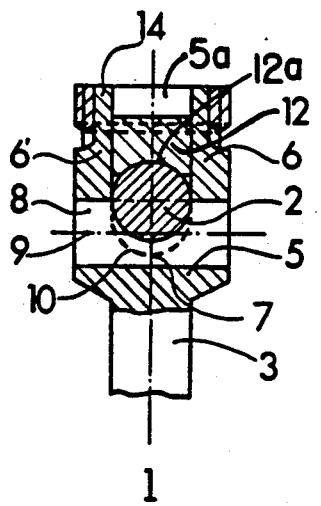
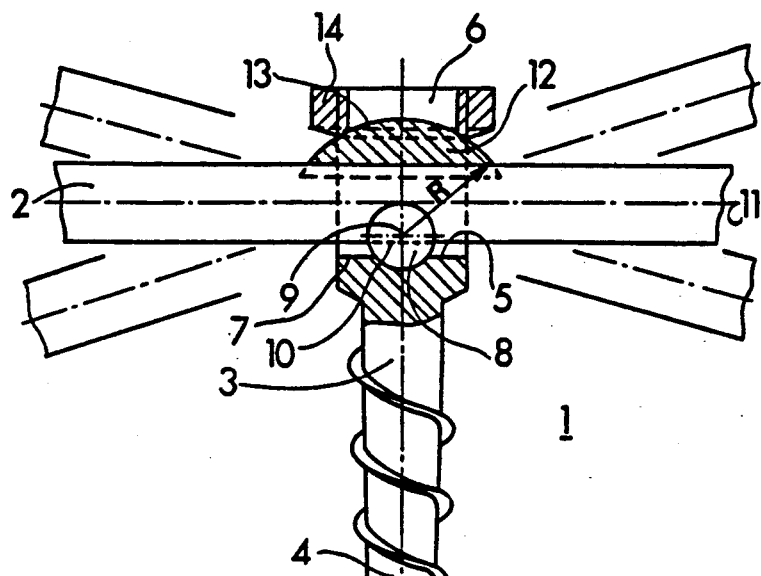
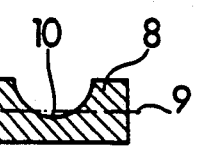
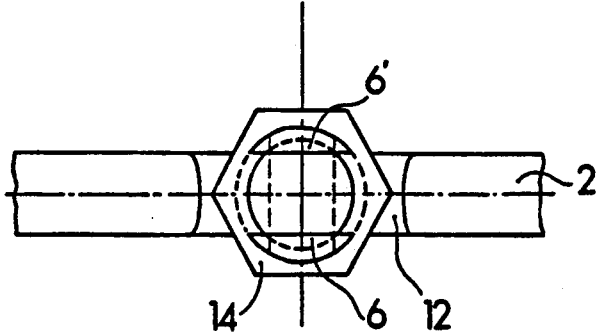

5,190,543

ANCHORING DEVICE

FIELD OF THE INVENTION

This invention concerns an anchoring device for use in treatment of the spine.

BACKGROUND

Anchoring devices of the type here concerned are components of systems that are used in surgery chiefly to stabilize posteriorly spinal column segments. They are designed either as pedicle screws, which are inserted through the pedicles into the vertebral body, or as hooks that are attached to the column by their blades. In either case, they are linked to longitudinal members (support rods or the like). By means of such systems, the vertebrae concerned are maintained at a distance from one another, or are compressed or maintained in traction. Depending on the design of the anchoring device, the connection to the longitudinal member may have several degrees of freedom, which can be fixed with a one or more elements.

The aim, as regards the use of pedicle screws, is to ensure a tension-free connection and an active anatomical repositioning. Depending on the design, the rotation of the pedicle screw in the plane defined by the longitudinal axes of the pedicle screws and the support rod can be blocked before, after or simultaneously with the sliding movement along the longitudinal member.

The aim, as regards the use of hooks, is to ensure a correct anatomical positioning of the hook. Depending on the design, the rotation of the hook can be blocked before, after or simultaneously with the sliding movement along the longitudinal member. The hooks are inserted or engaged, as necessary, cranially (lamina or transverse process) or caudally (pedicle or lamina).

The following requirements arise in the operating-room installation of such anchoring devices:

It must be possible to install the devices together with the rods in a manner that is simple and quick, in order to spare the patient avoidable operating time;

In the installation, the anchoring components (pedicle screws or hooks) must exert no undesired forces or moments on the bearing bone parts.

A large number of such anchoring devices exist, which aim at the two aforementioned qualities. Two of these solutions may be considered significant to the present invention.

DE-GM 8 915 443 describes an anchoring device in which a holder for the support rod, which holder is connected with the element that effects attachment to the bone, is U-shaped, and has an internal thread. A support rod is inserted into the U-shaped holder. A stop is then screwed into the internal thread against the rod. The underportion of the stop and/or the rod has a surface quality such as to ensure a firm connection between the stop, held by the internal thread, and the rod. This connection can be made very quickly during an operation. However, the rod can be tightened in only one direction, referred to the attachment element in the boney substance of the vertebra. If two attachment elements are therefore not very exactly aligned, something that is difficult to achieve, when the stops are tightened undesired stresses occur at both rod ends.

A device that constitutes an improvement over DE-GM 8 915 443 is described in EP-A1 0 300 881. This patent too involves a U-shaped holder in which the rod can be inserted after the pedicle screws have been positioned or the hooks have been engaged. This U-shaped holder has in the center of the vertex of the U a tip pointed toward the inside of the U, on which the rod comes to rest. At the top ends of the U a slider is positioned on the interior of the jaw. A part is inserted into this slider, which part has two screws that lie in front of and behind the tip on the axis of the rod and which can be turned against the axis. If the rod is resting on the two holder segments of the pedicle screws, by means of careful alternating turning of the four screws the rod can be attached to the pedicle screws without undesired stresses; however, this takes time and a certain skill in turning, if undesired stresses are to be prevented.

SUMMARY OF THE INVENTION

It is an object of the invention to create an anchoring device by means of which:

A connection between the pedicle screws (or hooks) and a support rod can be achieved simply and quickly, and Undesired stresses and moments when this connection is created can be prevented.

Fixation of all degrees of freedom with a single element.

These objects are obtained, in accordance with the invention by means of an anchoring device of the type described comprising a shank having a first end and a second end, means at said first end for attaching the shank to a bone, and a holder, comprising two jaw elements defining a U-shaped slot, at said second end for attachment to a support rod, a support element traversing the slot in said holder and having a recess to receive a support rod, said support element being capable of at least limited rotation to permit a support rod, seated in said recess, pivotal movement, a positioning element, having means to receive a support rod while permitting sliding movement of said rod relative to said positioning element, and retaining means threadly connected to said holder, said positioning element having a curved surface with the same center as the support element and said retaining means having a bearing surface for contacting said curved surface and pressing said positioning element against said rod, the action of said retaining means on said curved surface being such as to insure a stress-free connection between the anchoring device and the support rod.

The invention further includes a system comprising an anchoring device as described, or a plurality of such devices, and a support rod.

The invention will be further described with reference to the accompanying drawing. The drawing illustrates an embodiment of the invention with a pedicle screw for attachment to the bone. All advantages of the invention can also be achieved in an embodiment with a hook, for example as described in DE-GM 8 915 443. This embodiment is not specifically shown.

BRIEF DESCRIPTION OF THE DRAWINGS

In the drawings:

FIG. 1a is a view in side elevation, partly in vertical section showing an anchoring device according to the invention and a support rod different pivotal positions.

FIG. 1b is a front elevational view, partly in vertical section of the holder of the device shown in FIG. 1a.

FIG. 1c is a top plan view of the device of FIG. 1a, showing also a support rod.

FIG. 1d is a cross section of the support element of the device of FIG. 1a.

FIG. 2b is a front elevation view, partly in vertical section of the modified version shown in FIG. 2a.

DETAILED DESCRIPTION OF A PREFERRED EMBODIMENT

Figure 2A:
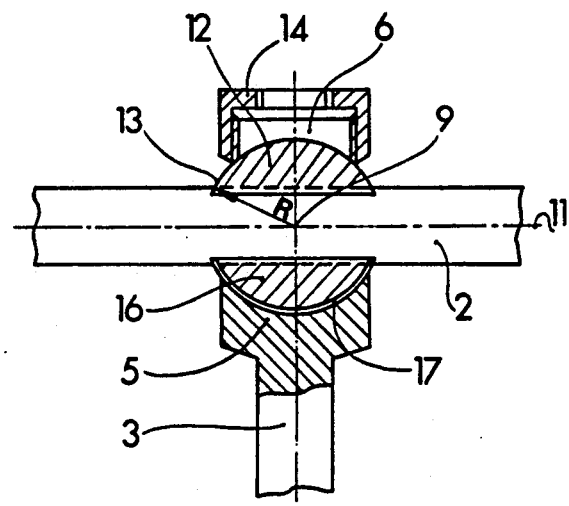
FIG. 2a is a side elevational view, partly in vertical section of a modified version of the device of FIGS. 1a to 1d.

Referring to FIG. 1a, the device is shown as a pedicle screw 3, it being understood the device might also be constructed as a hook. The screw 3 has a shank 4 which is threaded at one end. At the other end of the shank 4 is a holder 5. The holder 5 is formed by jaws 6,6' and has a slot 5a in the shape of a U, viewed in the direction of support rod 2. The shaped interior of the holder 5 has an apex line 7. A support element in the form of a pin 8 is inserted transversely through the jaws 6,6', perpendicular to the axis 18 of the shank 4 and to the apex line 7. The pin 8 has a longitudinal axis 9 and, perpendicular to its axis, a recess 10. The recess 10 has a cross section shaped as the segment of a cylinder having the same radius as the rod which is to be attached to the device. Inserted into the U shaped slot 5a, the control rod 2 fits into this recess 10. The slot 5a extends below the bottom of recess 10. This permits the rod to be pivoted on the axis 9 of pin 8 as far as is permitted by the difference between the depth of the slot 5a and the recess 10. The pin 8 thereby forms a support for rod 2, which permits rod 2 to be pivoted about axis 9.

During their attachment to the bone, two pedicle screws such as 3 are oriented by turning in such manner that rod 2 can be placed in recess 10 of pins 8 in the holder 5 of each screw. When the positioning is done, rod 2 pivots the transverse pins 8 of both screws until rod 2 reaches a position in which it is attached without stress to both pedicle screws.

For securing the support rod 2 to pedicle screw 3, a positioning element 12 and a retainer in the form of a nut 14 are provided. The positioning element 12 rests between jaws 6,6' of holder 5 on rod 2, and has on its side facing away from rod 2 a curved surface 13 that, when correctly positioned has a radius R to the axis 9 of transverse pin 8. To facilitate assembly of the positioning element 12, a center tapped hole (not shown) can be provided, into which an auxiliary tool, e.g. a threaded rod, can be temporarily inserted.

The installation of the positioning element 12, and the attachment between rod 2 and pedicle screw 3, is achieved with the help of the nut 14, which is screwed on an internal or external thread on jaws 6,6' of holder 5. The surface of the bottom edge of this nut 14 is shaped in such way that when the nut 14 is turned on the threaded portion of the holder 5, the positioning element 12 slides initially to the correct position on rod 2, in which all edge points of surface 13 lie on a radius R to axis 9 of transverse pin 8, with consequent facilitation of a stress-free attachment. Upon further tightening of nut 14, a clamping connection is created between positioning element 12 through its surface 12a, rod 2 the transverse pin 8, and the holder 5, and rod 2 is thereby attached without stress to pedicle screw 3.

Figure 2B:
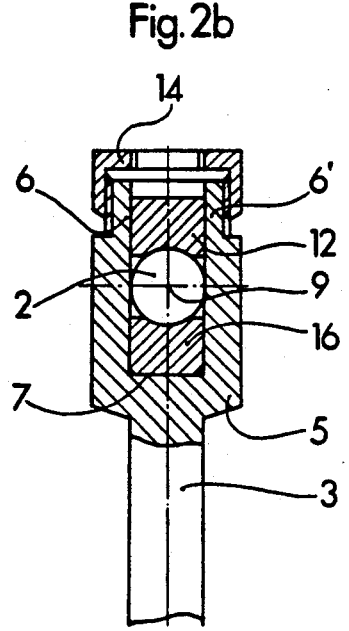

A variant of the invention is shown in FIG. 2. Here the rotational axis 9 is at the level of the axis 11 of upper rod 2. Instead of transverse pin 8, which in FIG. 1 is inserted laterally into holder 5, here a support element 16 is inserted from the top into the holder 5. The element has the same qualities as the above-described positioning element 12. It has a cylindrical surface 17, which similarly has a radius R to rotation axis 9.

The support element 16 and positioning element 12 can alternatively be constructed in such manner that their surfaces 13, 17 are parts of a sphere, the center point of which lies on rod axis 11 and rotation axis 9. In this case the bottom of slot 5a of holder 5 must be similarly spherical. The rotation axis 9 then degenerates into a rotation point. In the embodiment described here, with a pedicle screw 3 as the means for attachment to the bone, this variant offers no special advantages, since the pedicle screw 3 can rotate free on its longitudinal axis 18. In an embodiment with a hook as the attachment means, in contrast, this variant offers special advantages.

Lastly, the bottom and top formed parts 16 and 12 can be joined along one of their longitudinal sides, the result being a one-piece slotted part, open on the other longitudinal side, which part can be pushed as a unit on rod 2.

Figure 3:
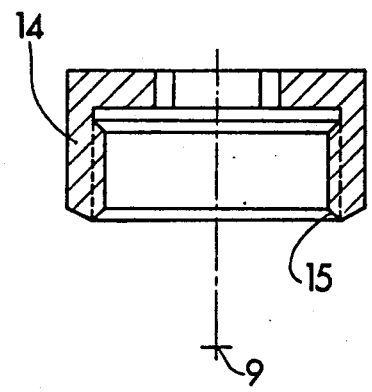
FIG. 3 is a view in vertical section of a nut for use in a device according to the invention.

The nut 14 illustrated in FIG. 3 has an oblique, rotation-symmetrical interior edge surface 15, which, when the positioning element 12 is in the correct position, comes to rest against surface 13 of element 12, which is delimited as steeply as possible against rod axis 11. Therefore, when screwed onto the threads of jaws 6,6', the nut necessarily pushes the positioning element 12 onto rod 2 in the correct position. The bottom edge of nut 14 is advantageously of a smooth, hard material that can slide, and which is harder than surface 13 of positioning element 12. If the nut 14 is now tightened slightly, nut 14 cuts or presses into element 12, and clamps rod 2, transverse pin 8, or element 16 and holder 5, so that a stress-free attachment is created between rod 2 and pedicle screw 3.

Alternatively, the edge surface of nut 14 can be made softer the surface 13.

The uncoupling of the degree of freedom of the anchoring device can be done in three different ways:

Use of a threaded rod together with a positioning element with a smooth curved surface and a threaded recess for the rod (blocking of translation before rotation);

Use of a smooth rod with a positioning element with a structured curved surface, for example a surface with ribs and a smooth recess for the rod (blocking of rotation before translation);

Use of a smooth rod with a smooth formed positioning element (uncoupling possible only with additional tools).

The anatomical repositioning includes, on the one hand, the straightening of the vertebrae (rotation in the sagittal plane) and on the other hand compression or traction, which can be done before or after the straightening of the vertebrae and left and right separately. Through uneven traction and/or compression left and right, a rotation of the vertebra in the frontal plane can also be achieved.

Methods for achieving compression or traction include:

a) Use of spreader and compressor (with a device known as a rod blocker);

b) The rod has a right and left (separate or cut one above the other) thread and is turned; in this case surface 10 of transverse pin 8 or the support element 16 must have the appropriate threading;

c) The rod has a thread with which compression or traction is achieved by means of appropriate nuts; and d) Use of two rods with right or left threading; the connecting nut contains both a left and a right threading, one above the other.

The anchoring device according to the invention is easy to use during an operation, and its use does not require much time. Because of its construction, no undesired stresses can occur between the pedicle screw 2 and the rod 2, and active anatomical resetting is possible.

Compared to various known devices, the anchoring device according to the invention has an additional degree of freedom (in the case of the embodiment with spherical formed parts two additional degrees of freedom). Another advantage is that it can be connected with rod 2 either directly or through a connecting member (for example, a member according to European patent application 90116070.5). It thereby becomes possible to minimize the number of elements and the distances between rod 2 and pedicle screws 3.

I claim:

1. An anchoring device for use in the stabilization of vertebral column segments comprising a shank having a first end and a second end, means at said first end for attaching said shank to a bone and a holder comprising two jaw elements defining a U-shaped slot between them at said second end for attachment to a support rod, a support element traversing the slot in said holder and having a recess for receiving a support rod, said support element being capable of at least limited rotation to permit a support rod, seated in said recess, pivotal movement, a positioning element having means to receive a support rod and retain such a rod while permitting sliding movement of the rod relative to the positioning element, retaining means threadedly connected to said holder, said positioning element having a curved upper surface and said retaining means having bearing surfaces for contacting said upper surface and pressing said positioning element against said rod, the action of said retaining means on said upper surface being such as to insure a stress-free connection between the anchoring device and the support rod.

2. The anchoring device claimed in claim 1, wherein the support element is a transverse pin.

3. The anchoring device claimed in claim 2, wherein the transverse pin is positioned laterally in the holder and has a recess in the shape of a segment of a cylinder having the same radius as the support rod to be held, and wherein the positioning element has a cylindrical contact surface.

4. The anchoring device claimed in claim 1, wherein the support element is shaped to receive the lower part of a support rod.

5. An anchoring system for the stabilization of vertebral column elements comprising a support rod and an anchoring device as claimed in claim 1.

6. The anchoring system claimed in claim 5 wherein the support rod is positioned in said support element so that it may be pivoted about an axis which intersects its longitudinal axis and the support element is positioned with a cylindrical surface facing the positioning element in the holder.

7. The anchoring system claimed in claim 5, wherein the support rod is capable of pivoting in two orthogonal directions.

8. The anchoring system claimed in claim 5 wherein the support element and the positioning element each have a spherical surface, the support element is positioned in the holder, with its spherical surface in contact with the holder, and the two spherical surfaces have a common center which lies on the longitudinal axis of the support rod.

9. The system claimed in claim 5 and including two anchoring devices linked together by a support rod.

10. The anchoring device claimed in claim 1 wherein the support and positioning elements are slotted and form a single unit.

11. The anchoring device claimed in claim 1 wherein said retaining means is a nut having threads adapted to engage threads on said jaw elements, said nut having an edge surface shaped for relative sliding movement with respect to the curved surface of the positioning element, so that said positioning element may be displaced into a position in which it is adapted to fix a support rod positioned in said holder with relation to the axis about which said support rod may pivot.

12. The anchoring device claimed in claim 11 wherein edge surface of the nut is smooth and is made of a material that is softer than the curved surface of the positioning element.

13. The anchoring device claimed in claim 12 wherein the curved surface of the positioning element is squared off.

14. The anchoring device claimed in claim 11 wherein the nut is made of a harder material than the curved surface of the positioning element.

15. The anchoring device in claim 1 wherein the curved surface of the positioning element is smooth.

16. The anchoring device claimed in claim 1 where the curved surface of the positioning element is structured.

17. The anchoring device claimed in claim 1, wherein the positioning element has a slot with a smooth lower surface to receive a support rod.

* * * * *